United States Patent [19]

Davies et al.

[11] Patent Number: 5,452,600
[45] Date of Patent: Sep. 26, 1995

[54] CALIBRATED VAPOR GENERATOR SOURCE

[75] Inventors: John P. Davies; Ronald A. Larson, both of Idaho Falls; Lorenzo D. Goodrich, Shelley; Harold J. Hall, Idaho Falls; Billy D. Stoddard, Idaho Falls; Sean G. Davis, Idaho Falls; Timothy G. Kaser, Idaho Falls, all of Id.; Frank J. Conrad, Albuquerque, N.M.

[73] Assignee: Lockheed Idaho Technologies Company, Idaho Falls, Id.

[21] Appl. No.: 129,635

[22] Filed: Sep. 29, 1993

[51] Int. Cl.⁶ .................................................. G01D 18/00
[52] U.S. Cl. ............................................ 73/1 G; 261/96
[58] Field of Search ................................ 73/1 G; 261/96

[56] References Cited

U.S. PATENT DOCUMENTS

| | | | |
|---|---|---|---|
| 3,521,865 | 7/1970 | Kertzman | 73/1 G X |
| 3,665,748 | 5/1972 | Mator | 73/1 G |
| 4,063,446 | 12/1977 | Fuhrmann | 73/1 G |
| 4,164,864 | 8/1979 | Schlereth et al. | 73/1 G |
| 4,905,497 | 3/1990 | Shindo et al. | 73/1 G |
| 5,092,217 | 3/1992 | Achter et al. | 73/1 G X |
| 5,213,769 | 5/1993 | Whitlock | 73/1 G X |
| 5,214,952 | 6/1993 | Leggett et al. | 73/1 G |
| 5,239,856 | 8/1993 | Mettes et al. | 73/1 G |
| 5,294,730 | 3/1994 | Succi et al. | 261/130 |
| 5,343,747 | 9/1994 | Rosem | 73/29.01 X |

FOREIGN PATENT DOCUMENTS

| | | | |
|---|---|---|---|
| 124790 | 9/1979 | Japan | 73/1 G |
| 607131 | 5/1978 | U.S.S.R. | 73/1 G |
| 648929 | 2/1979 | U.S.S.R. | 73/1 G |
| 13253 | 8/1992 | WIPO | 73/1 G |

Primary Examiner—Thomas P. Noland
Attorney, Agent, or Firm—Hopkins Roden Crockett Hansen & Hoopes

[57] ABSTRACT

A portable vapor generator is disclosed that can provide a controlled source of chemical vapors, such as, narcotic or explosive vapors. This source can be used to test and calibrate various types of vapor detection systems by providing a known amount of vapors to the system. The vapor generator is calibrated using a reference ion mobility spectrometer. A method of providing this vapor is described, as follows: explosive or narcotic is deposited on quartz wool, placed in a chamber that can be heated or cooled (depending on the vapor pressure of the material) to control the concentration of vapors in the reservoir. A controlled flow of air is pulsed over the quartz wool releasing a preset quantity of vapors at the outlet.

13 Claims, 6 Drawing Sheets

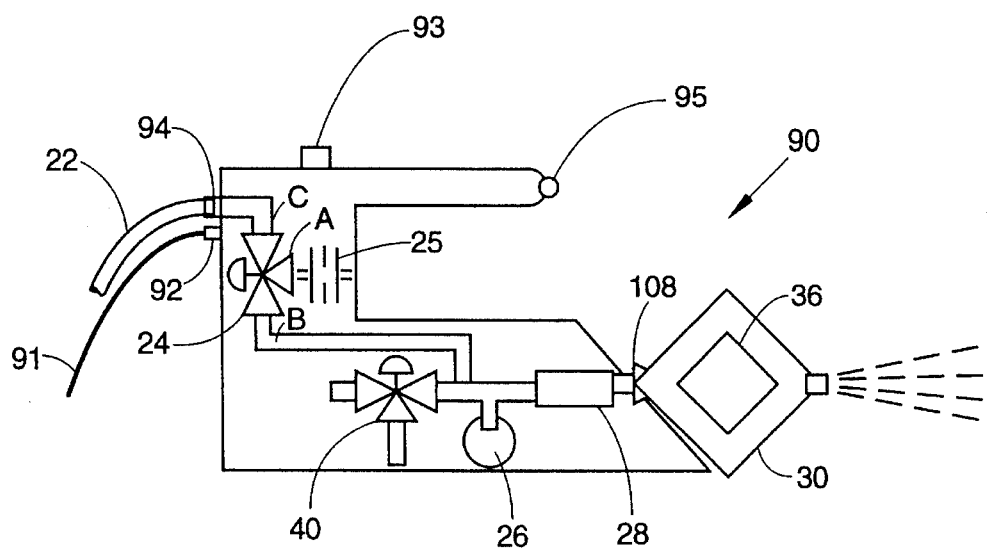
Figure 5
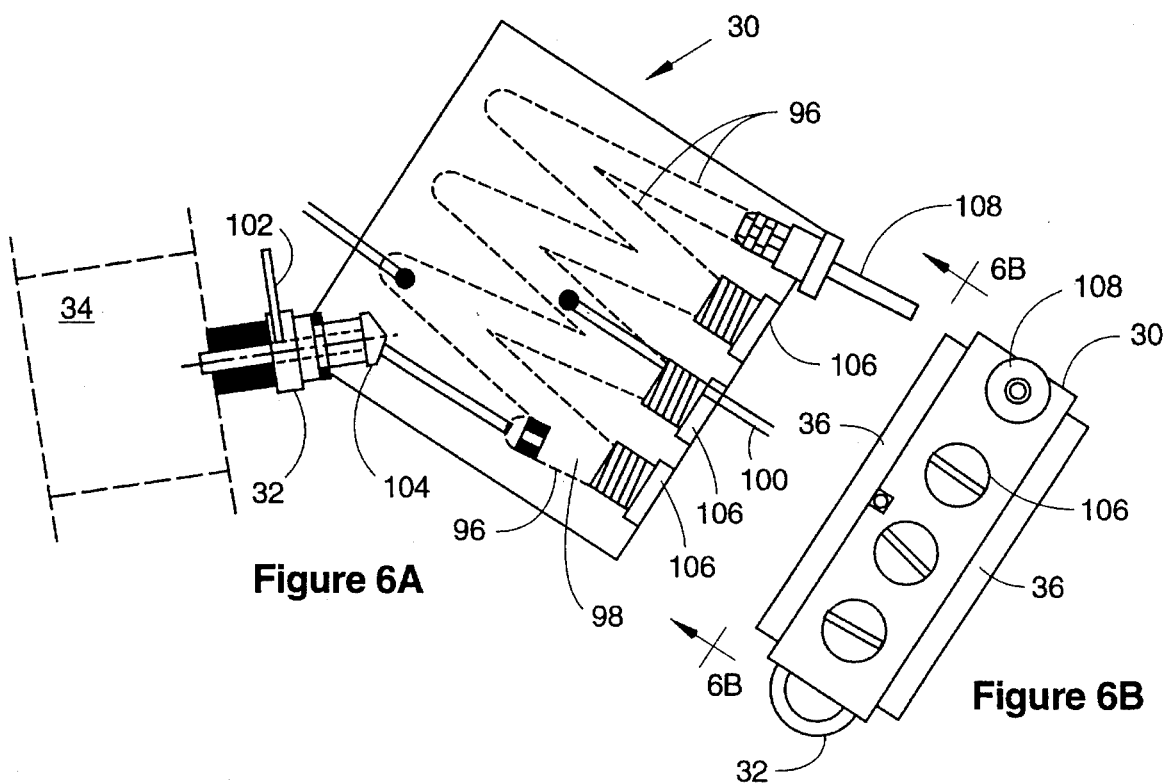
Figure 6A
Figure 6B

CALIBRATED VAPOR GENERATOR SOURCE

CONTRACTUAL ORIGIN OF THE INVENTION

The United States Government has rights in this invention pursuant to Contract No. DE-AC07-76ID01570 between the U.S. Department of Energy and EG&G Idaho, Inc.

FIELD OF THE INVENTION

This apparatus and method will provide a controlled source of vapors to test and calibrate various types of vapor detection systems. A source substance is coated on quartz wool and contained in a reservoir. The reservoir is heated or cooled (depending on the vapor pressure of the source) with a controlled thermoelectric heater/cooler releasing a quantity of substance molecules into a pulsed air stream which can be calibrated with a spectrometer or other analytical instrument.

BACKGROUND OF THE INVENTION

There is an increasing need for detection of very low level concentrations of narcotic and explosive vapors. Security personnel in airports and other sensitive areas are currently using apparatus that sense these vapors in the parts per trillion (ppt) range. At the present writing, the National Institute for Standards and Technology does not have standards for explosive vapors; therefore, a portable calibrated vapor generator source is critically needed in the field to test and calibrate those vapor detection devices such as that disclosed in U.S. Pat. No. 5,157,261 issued Oct. 20, 1992, which uses fiber optic spectroscopy and changes in fluorescence to detect explosives. U.S. Pat. No. 4,820,920 issued Apr. 11, 1989, discloses a second method and apparatus for detecting explosive or illegal drugs by microwave or RF radiation and then injecting the substance into a mass spectrometer for spectrum analysis.

It is desirable to be able to test and calibrate these type devices in the field to determine operability and accuracy at low concentrations. It is therefore the purpose of this invention to describe an apparatus and method for calibrating these detection devices in the field using a portable calibrated vapor generator source.

SUMMARY OF THE INVENTION

The invention generally stated is a calibrated vapor generator apparatus comprising:

a pressurized clean air supply;

means for controlling the flow of pressurized clean air in communication with the clean air supply;

means for controlling a pulse time for the flow of pressurized air in communication with the means for controlling the flow of the pressurized clean air;

a reservoir means for desorbing a known quantity of a vapor source substance in communication with the means for controlling the pulse time;

means for sensing and indicating the quantity of vapor source substance desorbed from the reservoir means by an electronic integrator/controller thereby providing a calibrated pulse of vapor to a vapor detection device.

Additionally, this invention discloses a method of using the apparatus for providing a controlled and known source of vapors to test and calibrate vapor detection systems, comprising the steps of:

coating a carrier with a known quantity of a vapor source substance;

placing the carrier within a reservoir;

controlling a temperature within the reservoir;

passing a pressure controlled clean air pulse through the reservoir;

measuring the pressure and duration time of the pulse;

integrating the pressure as a function of time of the pulse; and then indicating a weight of the vapor source substance, thereby providing a known quantity to test and calibrate the vapor detection system.

Other objects, advantages, and capabilities of the present invention will become more apparent as the description proceeds.

BRIEF DESCRIPTION OF THE DRAWINGS

The invention may be better understood and further advantages and uses thereof may become more readily apparent when considered in view of the following detailed description of the exemplary embodiments, taken with the accompanied drawings, in which:

FIG. 5 is a diagramic view of the hand-held vapor generator head;

FIG. 6A is a plan view of the quartz wool reservoir and attached thermoelectric heater/cooler;

FIG. 6B is a side view of the reservoir taken through lines 6B of FIG. 6A;

DETAILED DESCRIPTION OF THE INVENTION

Figure 1:
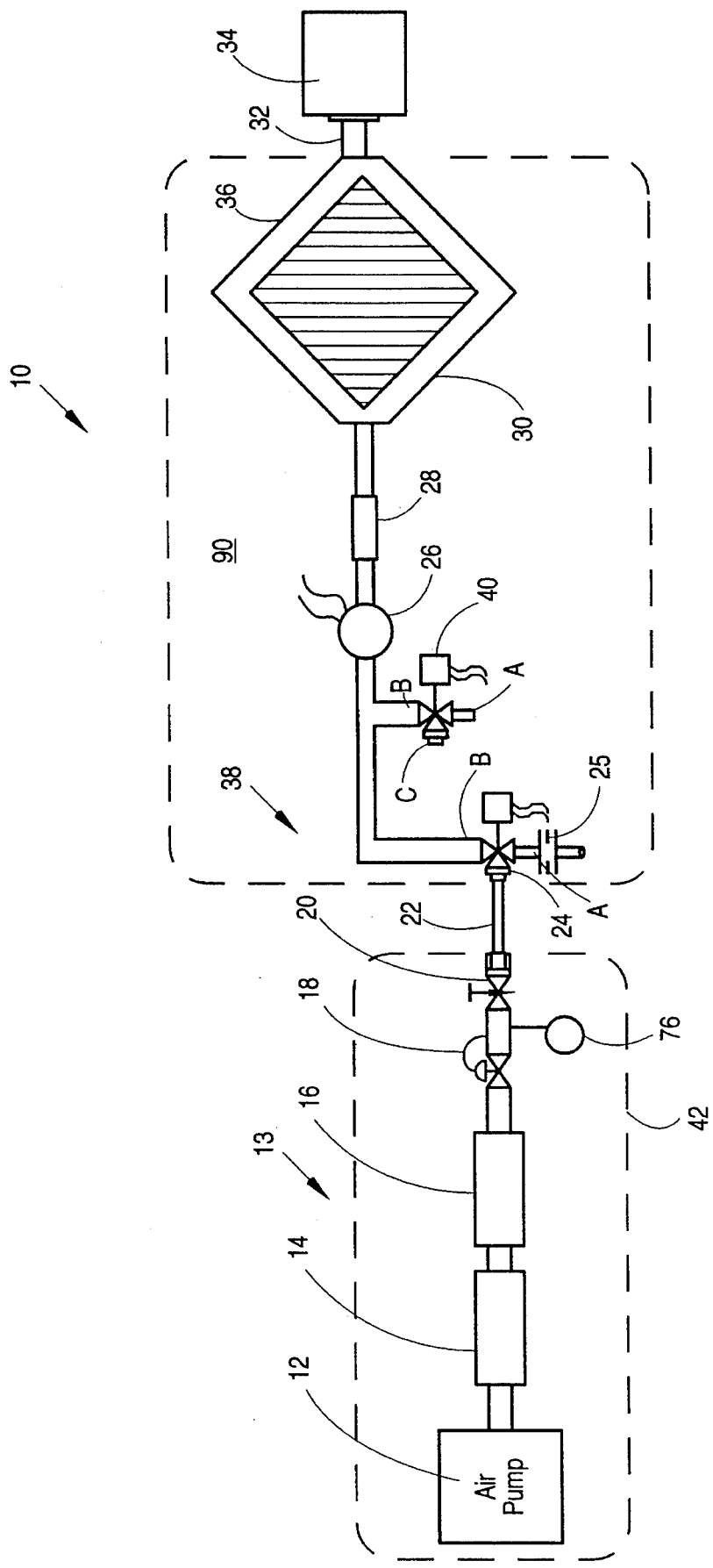
FIG. 1 is a piping schematic drawing of the vapor generator.
Figure 2:
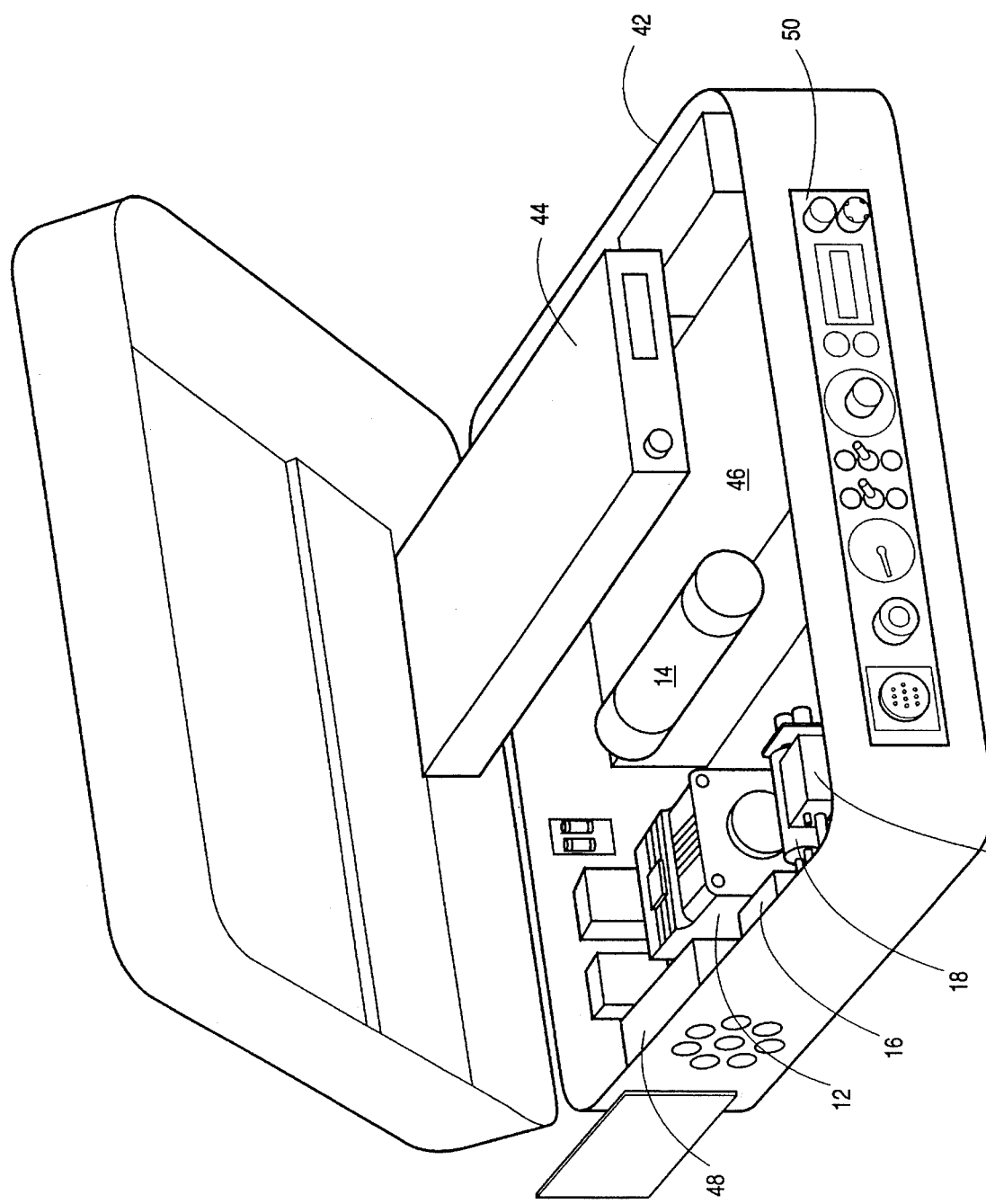
FIG. 2 is a perspective view of the portable vapor generator case.
Figure 3:
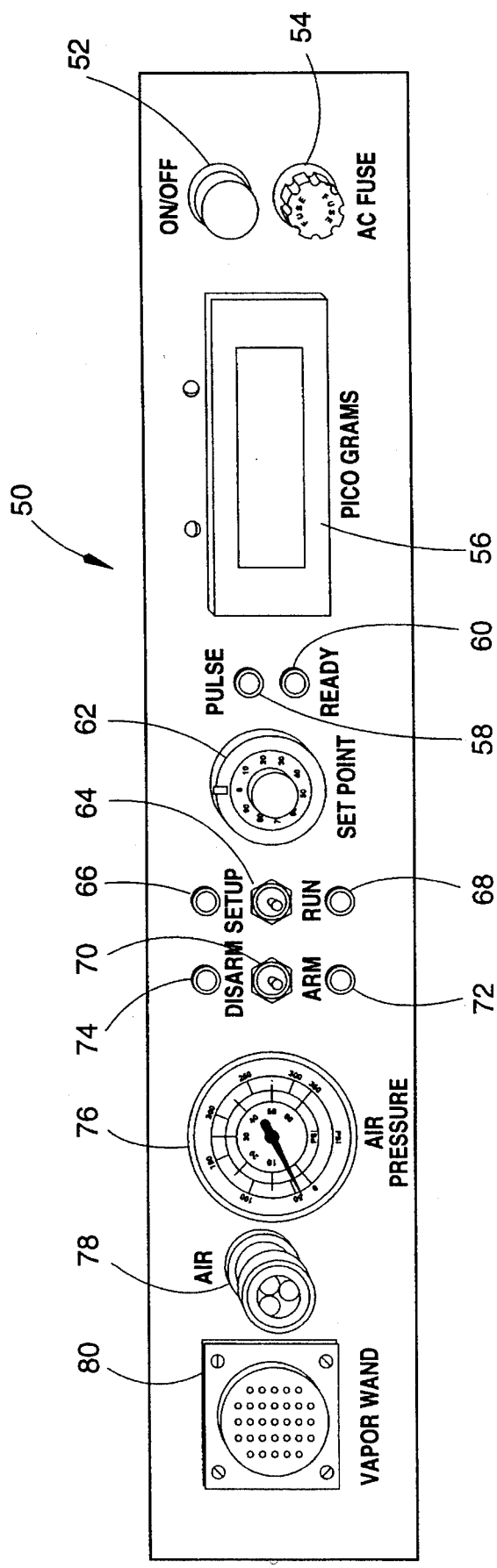
FIG. 3 is a front view of the generator control panel.
Figure 4:
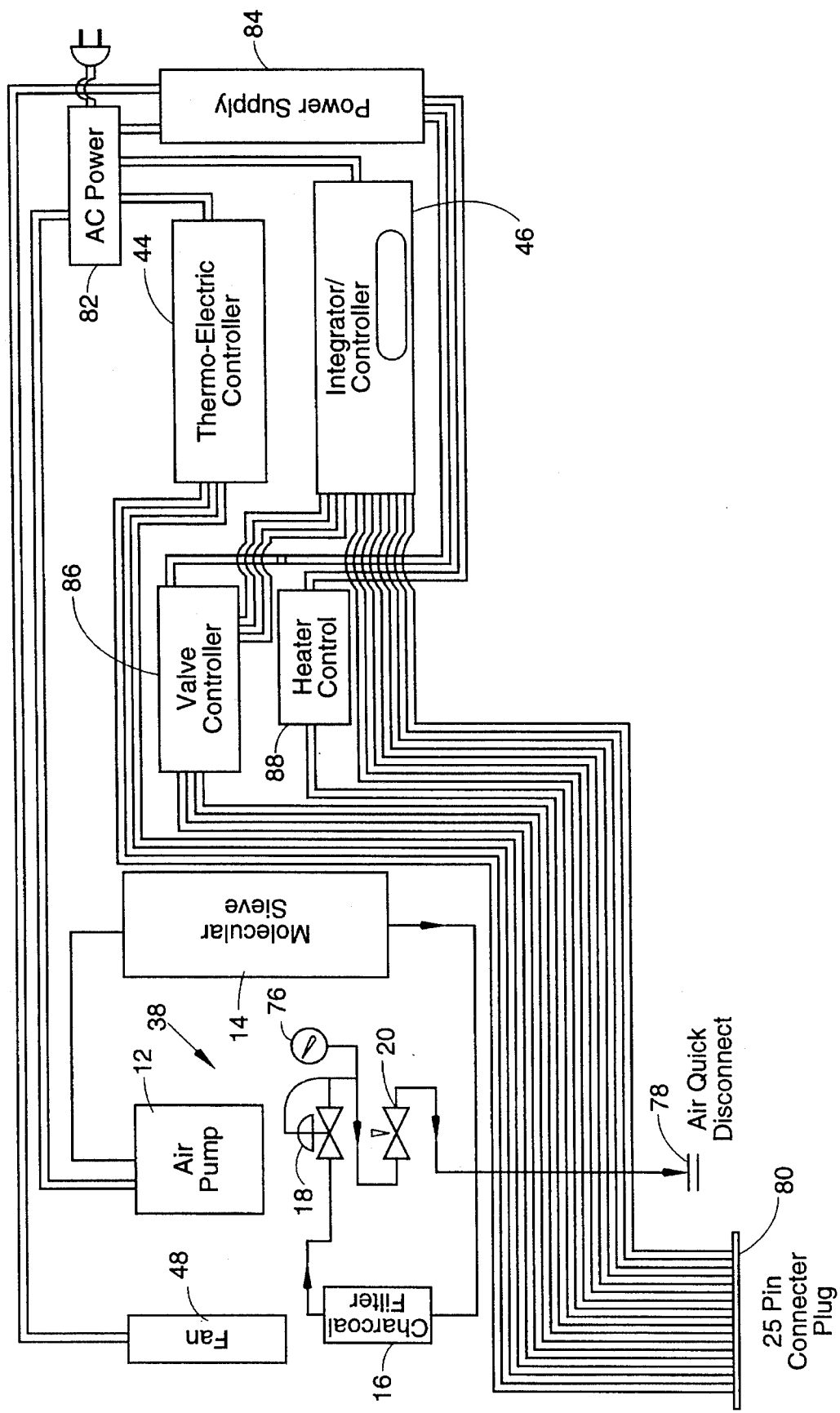
FIG. 4 is an electrical and piping block diagram.

Referring to FIG. 1, the vapor generator apparatus 10 is shown in schematic form. The clean source of air is provided by pump 12 and piped to filter assembly 13 consisting of a molecular sieve 14 which is a moisture filter and a first activated charcoal filter 16 to remove hydrocarbons. The pressure regulator 18 and flow control valve 20 maintain specific air flows by carefully controlling the pressure. The air flow is first set up by passing air through a flexible 5' tubing 22 and out vent port A of 3-way solenoid valve 24. The flow is properly set through port A by set-flow orifice 25. The solenoid valve 24 then directs air to port B, a pressure transducer 26, a second activated charcoal filter 28, and into the quartz wool reservoir 30. It is within the reservoir that the source vapor is desorbed from the quartz wool into the passing air stream, exiting through exit heater 32 into an adjacent vapor detector 34 (shown in phantom), which is being calibrated. The amount of vapors exiting the generator 34 is controlled by a pair of thermoelectric heater/coolers 36 and the length of time and pressure in the flow-control means 38, i.e., the integral of pressure over time. This is presented in the following formula:

$$\text{Picograms} = K \int_0^T dp \, dt$$

Where the weight in picograms of gas is proportional to the integral of differential pressure over time. One heater/cooler is on the front of reservoir 30 as shown, the other on the back. This time T is controlled by completing a pulse of air flow when closing 3-way valve 24 port C and opening 3-way vent valve 40 to port C.

The thermoelectric heater/coolers 36 operate to heat or cool the reservoir 30 depending on which chemical source is on the quartz wool, e.g. TNT would require a temperature of about 20° C., RDX a temperature of about 70° C., and PETN a temperature of about 65° C.

Figure 7:
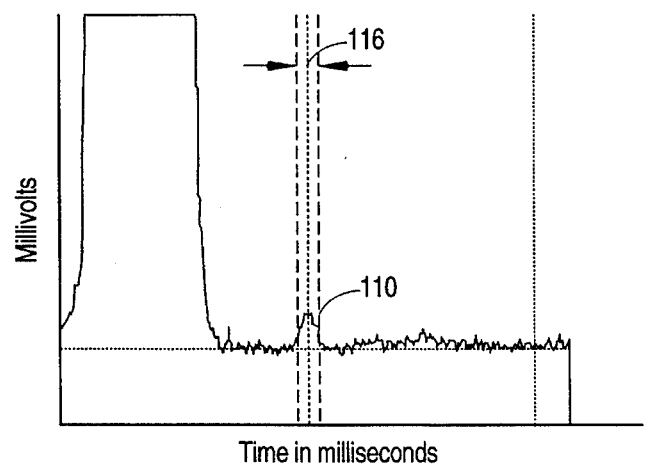
FIG. 7 is a typical TNT spectra from a calibration check using an ion mobility spectrometer (IMS)
Figure 8:
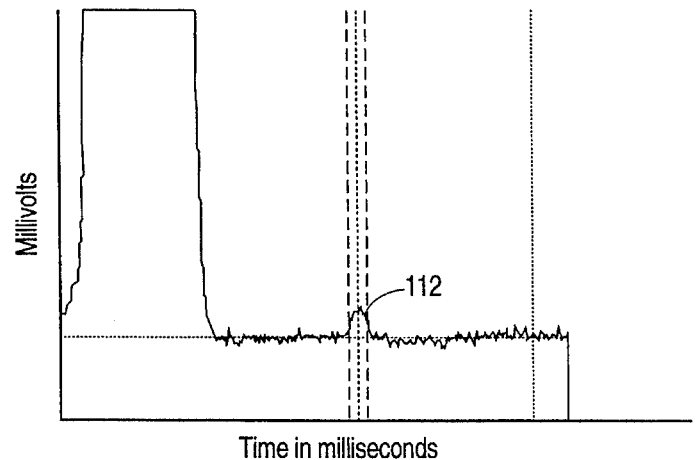
FIG. 8 is a typical RDX spectra using the IMS.
Figure 9:
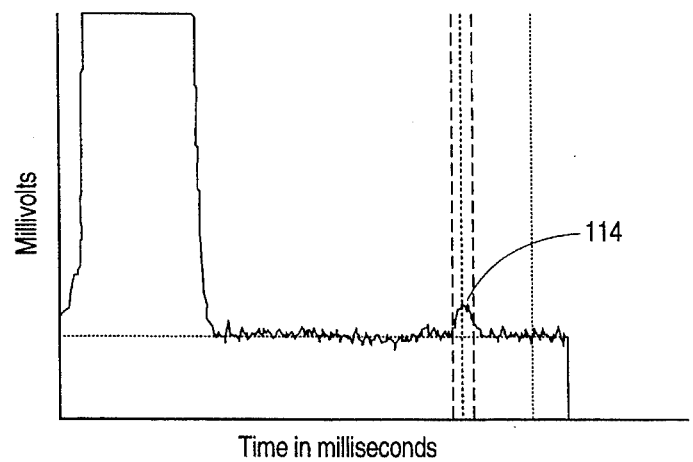
FIG. 9 is a typical PETN spectra using the IMS.

In this apparatus, the air pump 12, sieve 14, filter 16, pressure regulator, and flow controller are contained within case 42 (shown in phantom) and the remaining components are contained within a "head" 90 as will be described later. The umbilical connection being made by Teflon™ tube 22.

Referring now to FIG. 2, one can see some of the internal components within case 42. In addition to the air pump 12, sieve 14, filter 16, pressure regulator 18, and flow control valve 20, there are electrical devices consisting of thermoelectric controller (TEC) 44 that controls the thermoelectric heater/coolers, electronic integrator/controller 46, and an electric cooling fan 48 that cools the air compressor 12 and electrical devices. The controls for these various components are located on front cover control panel 50 and will be described by referring to FIG. 3.

FIG. 3 illustrates the details of control panel 50. From right to left, the devices are: a power on/off push button switch 52 and fuse 54, a source weight digital readout indicator 56, a pulse indicator light 58 and ready indicator light 50, a set point control (potentiometer) 62, a setup/run control switch 64 and setup indicator light 66 and run indicator light 68, an arm/disarm switch 70 and arm indicator light 72 and disarm indicator light 74, an air pressure gage 76, an air quick disconnect coupling 78, and a vapor head (wand) electrical plug 80.

FIG. 4 is an electrical and piping block diagram illustrating the components contained within case 50. Incoming AC power 82 is connected to a power supply 84 electronic integrator/controller 46, thermoelectric controller 44, and air pump 12. The power supply 84 provides power to the solenoid valve controller 86, the heater controller 88, and fan 48. Electrical outputs (and some inputs) connect between the 25-pin electric plug 80 and the thermoelectric controller 44, the valve controller 86, the heater controller 88, and the integrator/controller 46. The air pump 12 and air flow control means 38 discharge clean air to the air quick-disconnect coupling 78.

FIG. 5 discloses the components within the interchangeable head 90 which connects by electric cable 91 and flexible tubing 22 to the case. There are also quick disconnects for the cable at 92 and tube disconnect at 94 similar to quick disconnect coupling 78 and plug 80 (FIG. 3). 0n or within the head 90 is: the 3-way solenoid valve 24 and connecting orifice 25, the 3-way vent valve 40, pressure transducer 26, and second charcoal filter 28. The reservoir 30 and attached heater/cooler 36 are connected to the filter 28 by a reservoir entrance fitting 108 and an INITIATE push button 95 that starts the air is located on the front of the head 90. A pair of LED lights 93 for READY and PULSE are on top of the head.

The details of the reservoir 30 can be seen in FIG. 6A, which is shown with the thermoelectric heater/cooler removed. The body of the reservoir 30 has been drilled to provide a series of six connecting apertures 96 (in phantom) which contain the substance coated quartz wool 98, i.e., TNT, RDX, PETN, or narcotics.

Thermistor 100 controls the temperature of the thermoelectric heaters 36 (FIG. 6B) and the exit heater 32, respectively. The exit heater 32 maintains the exit temperature about 2° above the reservoir to prevent the vapors from coating the exit tube. A 0.5 micron stainless steel frit 104 (composite filter) removes any particles from the air stream above 0.5 micron from the reservoir apertures 96. The carrier or quartz wool 90 is inserted in the apertures 96 and then coated with a methyl ethyl ketone (MEK) solvent containing the explosive (or methanol(MEOH) solvent containing a narcotic). The MEK or (MEOH) evaporates leaving the explosive or narcotic coating on the wool 98. Then, the end caps 106 and entrance fitting 108 are threaded into the reservoir 30.

FIG. 6B illustrates the thermoelectric heater/cooler 36 mounted on the reservoir 30.

In operation, the air pulse from the interchangeable head 90 (FIG. 5) enters at the entrance fitting 108 passes over the quartz wool 98 and exits the heater 32 into the vapor detector 34 that is being calibrated.

The overall apparatus operation will be described by referring to FIGS. 1, 2, and 3. It is assumed that the cables 91 and tube 22 are connected to the case 42 and head 90.

The system is activated by setting the arm/disarm switch 70 to DISARM and pushing the power ON button 52, which starts air pump 12, energizes the thermoelectric controller 44, thermoelectric heater/cooler 36, and exit heater 32. Check or set the temperature set point on the thermoelectric controller 94 to the desired ohms obtained from the thermistor resistance chart. Set the air pressure regulator 18 to 127+7-O K Pa (18+1-O psi). After a 10-minute warmup, set the run/setup switch 64 to RUN to check that the weight (picogram) meter 56 reads zero. Adjust the set screw above the meter as necessary and then set the run/set switch 64 to SETUP. Turn the set point potentiometer 62 to the desired setting as read on the picogram meter 56. Set the run/setup switch 64 to RUN and the arm/disarm switch to ARM. Check the READY LED lights, i.e., 60 on FIG. 3, and 93 on FIG. 5. Start the pulse by pushing the INITIATIVE push button 95 on the front of the head 90. The red PULSE light 93 on the head 90 and red PULSE light 58 on the control panel 50 will come on during the pulse. Readout the digital number on the picogram weight indicator 56.

Wait for the READY lights to come on before another INITIATE cycle.

The device being tested can now be readout or its alarm set point verified by comparing it to the picogram indicator 56. The picogram weight can also be mathematically converted to other units of measure, e.g., parts per trillion (ppt).

The technical specifications for the apparatus are as follows: calibrated to a reference instrument; picogram to nanogram output; variable temperature from 20°–80° C.; source temperature control ±0.1° C.; flow range 0–300 ccm; variable pulse width; interchangeable hand-held portable head, i.e., a different head for different explosives or narcotics; digital readout of mass outputs; size of case: 18 inches×13 inches×8.5 inches; weight of case: 33 pounds; and power: 110 volt AC.

FIGS. 7, 8, and 9 illustrate the results of calibration of earlier laboratory experimental vapor generator using three explosive vapors. Explosive mixtures can be made in the form of plastic explosives, which are made of an explosive chemical usually bound in a polymer matrix. Their main advantage is that they can be molded or cast into any desired shape or size. The explosive chemical is typically cyclonite (RDX), pentaerythritol tetranitrate (PETN), and trinitrotoluene (TNT) which have been used in this experimental lab setup. The machine used to calibrate the vapor generator is called an ion mobility spectrometer (IMS) which records the amount of time that it takes for an ion to travel to an electrified plate through a specific vapor, where the ion and vapor collisions slow down the ion mobility. The graphs of FIGS. 7, 8, and 9 show the millivolt output of the spectrometer versus time in milliseconds for the three explosives: TNT, RDX, and PETN, respectively. The three peaks 110, 112, and 114 are at 14.3 ms, 15.8 ms, and 18.8 ms, respectively. The retention times correspond to a specific IMS (PCP IMS 110) and specific conditions of 160° temperature and 646 torr atmospheric pressure.

The output from the IMS is monitored in a specified time window (typically 550 μs wide) as at 116, centered on the peak associated with the explosive to be quantified. The voltage in this window is integrated by an integrator and then subtracted from the integrated voltage in a background window. The background window is set close to the signal window in a region that is clear of extraneous peaks. This delta voltage is next sent to a second integrator. The integrator integrates the output voltage versus time. By integrating the area between the lines (about 550 nanoseconds on either side of the peaks) as at 116, the amount of substance can be accurately determined.

While a preferred embodiment of the invention has been disclosed, various modes of carrying out the principles disclosed herein are contemplated as being within the scope of the following claims. Therefore, it is understood that the scope of the invention is not to be limited except as otherwise set forth in the claims.

What is claimed is:

1. A calibrated vapor generator apparatus comprising:

a. a pressurized clean air supply;

b. means for controlling the flow of pressurized clean air in communication with the clean air supply;

c. means for controlling a pulse time for the flow of pressurized air in communication with the means for controlling the flow of the pressurized clean air;

d. a reservoir means for desorbing a known quantity of a vapor source substance in communication with the means for controlling the pulse time;

e. means for sensing and indicating the quantity of vapor source substance desorbed from the reservoir, said means further comprising a pressure transducer and an integrating circuit wherein the weight of the substance is proportional to the integral of air pressure over time and is indicated on an electronic readout device.

2. The apparatus as recited in claim 1 wherein the pressurized clean air supply comprises an air pump and connecting filter assembly.

3. The apparatus as recited in claim 1 wherein the means for controlling the flow of pressurized air comprises a pressure regulator and connecting flow control valve.

4. The apparatus as recited in claim 1 wherein the means for controlling the pulse time comprises a pair of 3-way solenoid valves in serial connection contained within an interchangeable head.

5. The apparatus as recited in claim 4 wherein the reservoir means is within the interchangeable head and comprises a temperature controlled body having a plurality of serial connected apertures containing a coating on quartz wool, said coating being the vapor source substance.

6. The apparatus as recited in claim 5 wherein the temperature of the body is controlled by a pair of thermoelectric heater/coolers affixed on opposing sides of the body and is controlled within 0.1° C.

7. The apparatus as recited in claim 1 wherein the vapor source substance is TNT, RDX, or PETN.

8. The apparatus as recited in claim 1 wherein the vapor source substance is an illegal drug.

9. A method for providing a controlled and known source of vapors to test and calibrate vapor detection systems, comprising the steps of:

a. coating a carrier with a known quantity of a vapor source substance;

b. placing the carrier within a reservoir;

a controlling a temperature within the reservoir;

d. passing a pressure controlled clean air pulse through the reservoir;

e. measuring the pressure and pulse time;

f. integrating the pressure as a function of time of the pulse; and then g. indicating a weight of the vapor source substance, thereby providing a known quantity to test and calibrate the vapor detection system.

10. The method as recited in claim 9 wherein the vapor source substance is TNT, RDX, or PETN and the carrier is a quartz wool.

11. The method as recited in claim 9 wherein the temperature within the reservoir is maintained by a thermoelectric heater/cooler to within ±0.1° C.

12. The method as recited in claim 9 wherein integrating the pressure and pulse time is performed by an electronic integrator/controller, a valve controller, a pair of solenoid valves, and a pressure transducer.

13. The method as recited in claim 12 wherein the clean air pulse is provided by an air pump, a filter assembly, a pressure regulator, and a flow control valve, through a tubing to and an interchangeable head containing the reservoir, solenoid valves, and pressure transducer.

* * * * *